United States Patent [19]

Thomas

[11] Patent Number: 5,100,111
[45] Date of Patent: Mar. 31, 1992

[54] DEVICE FOR THE DETECTION OF THE TEMPERATURE COURSE OF A METAL OR METAL ALLOY MELT USING MEASUREMENT TECHNIQUES

[75] Inventor: Friedrich W. Thomas, Gelnhausen, Fed. Rep. of Germany

[73] Assignee: Leybold Aktiengesellschaft, Hanau, Fed. Rep. of Germany

[21] Appl. No.: 516,646

[22] Filed: Apr. 30, 1990

[30] Foreign Application Priority Data

Jun. 19, 1989 [DE] Fed. Rep. of Germany ....... 3919920

[51] Int. Cl.$^5$ .............................................. C21D 11/00
[52] U.S. Cl. .......................................... 266/88; 266/99; 266/100
[58] Field of Search ...................... 266/87, 88, 99, 100

[56] References Cited

U.S. PATENT DOCUMENTS

| | | | |
|---|---|---|---|
| 2,223,408 | 12/1940 | Dietert | 136/234 |
| 2,975,225 | 3/1961 | Barbieri | 136/234 |
| 3,186,699 | 6/1965 | Grönegress | 266/87 |
| 3,204,460 | 9/1965 | Milnes | 73/295 |
| 3,343,823 | 9/1967 | Schmeiser et al. | 266/87 |
| 3,436,520 | 4/1969 | Anders et al. | 219/130 |
| 3,467,542 | 9/1969 | Nordlie | 374/139 |
| 3,622,678 | 11/1971 | Allen | 373/68 |
| 4,105,191 | 8/1978 | Charbonier | 266/88 |
| 4,396,792 | 8/1983 | Falk | 136/234 |
| 4,934,664 | 6/1990 | Brämer et al. | 266/88 |

FOREIGN PATENT DOCUMENTS

0552597 5/1975 U.S.S.R. ................ 266/88

OTHER PUBLICATIONS

Ward et al., "Practical Application of Infrared Thermal Inspection Techniques", AFS Transactions, pp. 127–136, 4-80.
Petrie et al., *Infrared Camera and Data Acquisition System in Doublet III,* Rev. Sci. Instrum. 56(6), 6-85.
Hine, *Temperature Measurement,* Foundry Management & Technology, pp. 25–31, 2-87.

*Primary Examiner*—S. Kastler
*Attorney, Agent, or Firm*—Weil, Gotshal & Manges

[57] ABSTRACT

The invention relates to a device for the detection with measuring techniques of the temperature course of a metal or metal alloy melt in a container (39) which is influenceable by a heating device (22 to 24) and a cooling device (33). The temperature course is herein detected via a thermal camera (49) which is directed toward the region of the solidification front (48) of the melt. The data supplied by the thermal camera (49) are used for the purpose of determining the thermal gradient along on a coordinate of the container (39) and to control the heating device (22 to 24) according to the thermal gradient. Moreover, the data supplied by the thermal camera (49) are used for the determination of the solidification velocity of the melt to regulate the cooling device (33) in accordance with this solidification velocity.

20 Claims, 4 Drawing Sheets

DEVICE FOR THE DETECTION OF THE TEMPERATURE COURSE OF A METAL OR METAL ALLOY MELT USING MEASUREMENT TECHNIQUES

The invention relates to a device for the detection using measurement techniques of the temperature course of a metal or metal alloy melt in a container which is influenceable by a heating device and a cooling device.

In the detection of temperatures there can be differentiated between a point-like and an areal temperature detection. In the point-like temperature measurement only the temperature at a particular point is of interest while other areas are without or only of slight significance. Examples for point-like temperature measurements are the medical fever measurements or the room temperature measurements for heating systems regulation devices. In areal temperature measurements it is important to ascertain the temperatures at several locations simultaneously to determine the course of temperature boundaries. To this end infrared cameras are often used which image whole areas and assign a temperature to each point of these areas. Examples for the areal temperature detection are in the field of medicine the early recognition of certain types of cancer or in the field of geology the climatic investigation of ground and water surfaces. The recording of a heat image on board a helicopter or an airplane gains quickly information regarding the temperature distribution of an extended area which could not be detected with point-like measuring methods.

While in the case of the point-like heat detection a heat-sensitive element is as a rule in contact with the medium to be measured, the areal temperature detection is nearly exclusively a contactless temperature measurement.

It is already known to apply for point-like temperature measurements expansion thermometers, thermoelectric couples, resistance thermometers or semiconductor thermometers and for the areal temperature detection radiation thermometers of heat image cameras.

In the production of high-grade metals or metal alloys in general a point-like temperature measurement of the melt is carried out to control particular control processes on the basis of the determined melt temperature. Therein primarily thermoelectric couples with protective tubes of ceramic are applied which are brought into contact with the melt (U.S. Pat. No. 2,975,225, U.S. Pat. No. 3,467,542, U.S. Pat. No. 4,396,792).

However, it is also known to detect solidification fronts and the like in melts by means of special thermoelectric couple arrangements (U.S. Pat. No. 3,204,460; FIG. 1a in U.S. Pat. No. 3,436,520, FIG. 4 in U.S. Pat. No. 3,622,678). In these cases the thermoelectric couples are also brought into contact with the melt itself.

Thermographs with which a heat image of moderately large areas can be generated, are likewise known as such.

It is moreover known to apply such thermographs in foundries and the like (A. Ward, D. R. Ferrell: Practical Application of Infrared Thermographic Inspection Techniques, America Foundrymen's Society Transactions, 1980, pp. 127 to 136; T. W. Petrie, J. T. Scoville: Infrared Camera and Data-Acquisition System in Doublet III, Rev. Sci. Instrum. 56 (6), June 1985, pp. 1156 to 1159; H. Heine: Temperature Measurement, FOUNDRY management and technology, 2, 1987, pp. 25 to 31; A. E. Torok, P. C. Wilson in Technology for Premium Quality Castings, Eds. E. Dunn, D. R. Durham, The Metallurgical Society, 1988, "Recent developments in aluminium foundry technology", p. 78). From the last-cited publication it is also known to detect the thermal gradients during the solidification in order to recognize casting errors.

The known television thermography apparatus operates as a rule with an optoelectronic scanning of the object surface. Therein the radiation being emitted by the objects in the near infrared range generates a charge image on an infrared-sensitive detector. By line-wise scanning of the charge image a signal is obtained in which the local differences in the radiation intensity are contained as a temporal sequence of amplitude fluctuations. On a monitor screen this video signal generates a luminance equivalent to the radiation intensity. An optically perceivable heat image originates. Thermography installations of this type operate approximately in a temperature range of 350° to 1700° C. which can be divided into several partial ranges through appropriate shutter and filter combinations. The temperature resolution is approximately 2° K.

In foundry technology, thermographs are used inter alia to recognize refractory linings in blast furnaces, smelting furnaces and foundry stoves without needing to interrupt operation. By means of infrared monitoring unplanned operating failures are also avoided in that faulty sites are recognized in the state of development before they bring about a production stop. Qualitative infrared data are moreover suited to point out energy loss sites.

A particular problem in the production of high-quality metals and metal alloys is the detection of the position and the velocity of progression of the crystallization front, in particular with directional solidification, i.e. of the transition from liquified to the solidified metal, because the temporal and the spatial progression of the crystallization process has a direct influence on the quality of the metals and metal alloys.

The invention is therefore based on the task of detecting the position and velocity of progression of the crystallization front by means of a thermography apparatus, which for example can be a vidikon television recording tube, a pyroelectrical heat image tube or a pyrotron or pysicon.

This task is solved according to the features of patent claim 1.

The advantage achieved with the invention comprises in particular in that through point-wise scanning of a casting mold surface or the like, temperature differences of the casting mold are recognized and by drawing on known mathematical relationships the solidification front of a molten metal and its progression can be determined.

BRIEF DESCRIPTION OF THE DRAWINGS

An embodiment example of the invention is represented in the drawing and will be described in greater detail in the following. Therein show:

In FIG. 1a is shown a cylindrical casting mold 1 in cross section which is disposed on a cooling plate 2 and contains in its interior a metal, a metal alloy or the like, the metal or the metal alloy respectively herein has three zones: the zone 3 in which the metal coming from above is still liquid, the zone 4 in which the metal cooled down by the cooling plate 2 has already solidified, and the zone 5, in which the liquid metal solidifies. The zone 5 is represented ideally as a horizontal line and is identical with the solidification front of the metal. In FIG. 1a is represented so to speak an instantaneous recording of the solidification process of a metal in which the solidification front 5 is approximately in the center. If according to example drawing 1a heating from above is discontinued and cooling takes place via the cooling plate, then the solidification front migrates continuously in the upward direction and specifically at a velocity $V_E$ indicated by an arrow 6 pointing upward. The velocity $V_E$ herein is a vector which has the direction of the Z-axis 7.

Figure 1A:
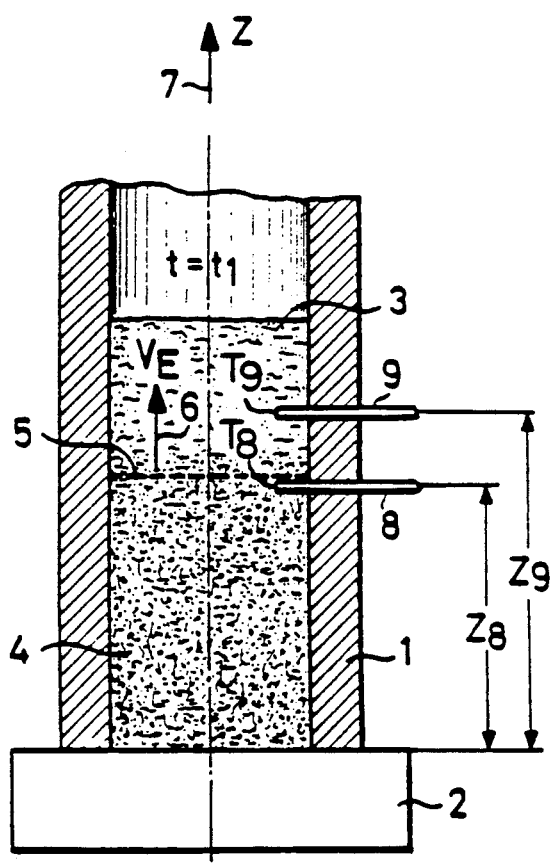
FIG. 1a a fundamental representation of a casting mold with a metal column which in the upper area is liquid and in the lower area solidified.

If all zones 3, 4, 5 are solidified, the cooling plate 2 can be removed and the metallic body enclosed by the casting mold 1, is taken from the casting mold. Closely below the solidification front 5 and on the right side of the casting mold 1 is provided a first thermoelectric couple 8 which is introduced with its one end into the already solidified zone 4 while its other end is located outside of the casting mold 1. The temperature at the inner end of the thermoelectric couple 8 is therein denoted by $T_8$. In corresponding manner the inner temperature $T_9$ of a second thermoelectric couple 9 is labeled which projects into the liquid zone 3 of the metal. The Z-coordinates of the two thermoelectric couples 8, 9 are given by $z_8$ or $z_9$ respectively.

These two point-like temperatures $T_8$, $T_9$ say only very little about the function $T=f(z)$, i.e. about the course of the temperature along the Z-axis. This temperature course is however of interest with alloys and specifically in particular the course of the solidification front 5 as a function of time.

Figure 1B:
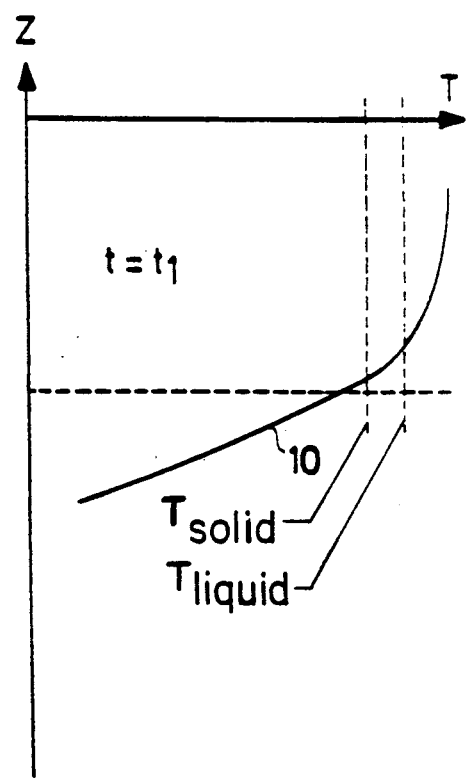
FIG. 1b a curve representation which shows the temperature course along the vertical axis of the casting mold.

In FIG. 1b is represented the function $T=f(z)$ at a given point in time, for example at time $t_1$. Curve 10 shows consequently the spatial temperature course in the casting mold 1 at time $t_1$ which applies also for the instantaneous recording of FIG. 1a. Stated differently: the curve 10 represents the function $T=f(z)_{t=t1}$. It can be seen herein that at the phase boundary 5 the gradient of the curve 10 is particularly pronounced. Combined with the solidification temperature $T_{sol}$ consequently the solidification front can be determined. By means of the two thermoelectric couples 8 and 9 curve 10 could not be determined since to do so would require a very large number of thermoelectric couples. With the two thermoelectric couples 8 and 9 it is at best possible to calculate a temperature gradient according to the formula $$\text{grad } T = \frac{T_9 - T_8}{\Delta z} = \frac{T_9 - T_8}{z_9 - z_8}$$

which, however, represents only a rough approximation. Only with an infinite number of thermoelectric couples arranged parallel to the Z-axis the temperature gradient $$\text{grad } T = \left(\frac{\partial T}{\partial z}\right)_{t=t1}$$

is obtained.

The cooling rate T of the entire metal cylinder in the casting mold 1 is greater the faster the solidification front 5 migrates upward. Consequently, $$\dot{T} = K \cdot V_E$$

applies where $V_E$ is the solidification front. The proportionality factor K corresponds herein to grad T so that for the cooling rate $$\dot{T} = \text{grad } T \cdot V_E$$

applies.

The cooling rate T before the solidification front is to be interpreted geometrically as the slope of the tangent at the time-temperature curve $T(t)$ at time-point $(t_2, T_1)$. The mean solidification velocity $V_E$ in the Z direction is calculated as approximation according to $$V_E \approx \frac{z_i - z_{i+1}}{t_i - t_{i+1}} + V_A(t_i)$$

wherein $z_i$, $z_{i+1}$ indicate oven-fixed coordinates of two measuring sites one lying above another and $V_A$ the actual value of the lowering velocity. The curve shown in FIG. 1b represents the conditions for the point in time $t_1$. It is understood that it is also possible to draw for any other point in time a space-temperature progression in the oven-fixed system z. The slope of the individual progressions at liquid temperature is then an approximation for the temperature gradient before the solidification front. The behaviour of the phase boundary 5 is a function of the particular material in the casting mold 1. Pure substances as well as eutectic alloys and mixtures change their aggregate state or their modification form with certain conversion temperatures characteristic for each type of substance; therein so-called latent heat or "conversion enthalpy" is released or stored. Non-eutectic alloys and mixtures show these phase change effects within one temperature interval and are therefore more difficult to treat mathematically. Overall, the mathematical description of solidification processes is also impeded through the migration of the area boundaries primarily, however, through a nonlinear phase boundary condition resulting from the local enthalpy conversion.

Figure 2:
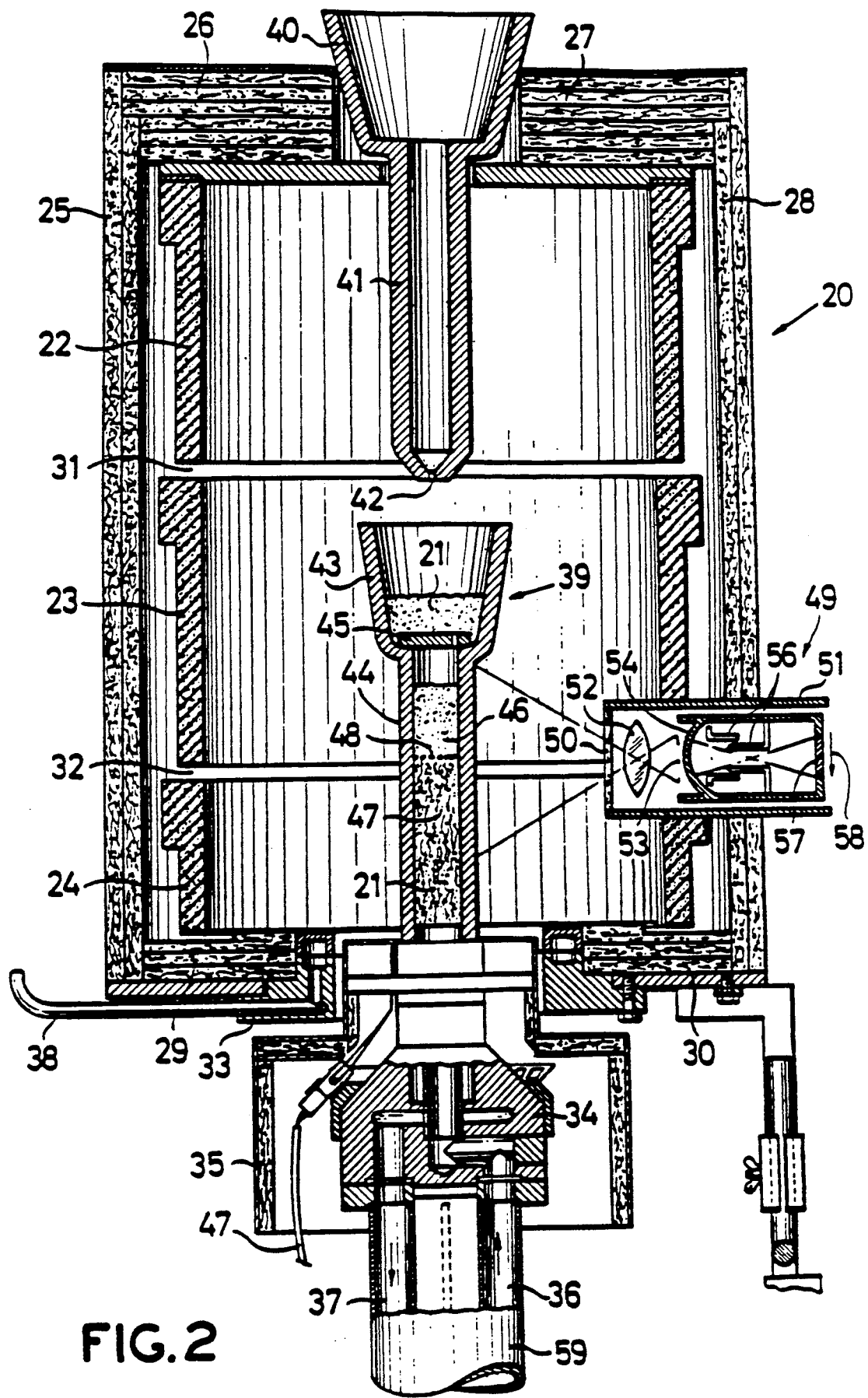
FIG. 2 a vacuum oven with attached infrared monitoring camera.

In FIG. 2 a sectional lateral view is represented of a vacuum oven 20 for the directed solidification of a melt 21. This vacuum oven 20 has for example three cylinder jacket-shaped graphite heating elements 22, 23, 24 which are protected against heat losses by an insulation 25 to 30. Between the heating elements 22 to 24 are provided gaps 31, 32 for reasons of electrical insulation.

The electrical connection of the heating elements 22 to 24 are not shown in FIG. 2. The heating elements 22 to 24 are required to maintain the melt 21 in a liquid state and to effect through a heat flow which is as much as possible one-dimensional a directed solidification of the melt 21. So that the temperature gradient required for the solidification of the melt 21 is definitively generated a cooling path 33 (baffle) is provided next to and below the insulation area 29, 30. Relative to this cooling path 33 a cooling head 34 can be vertically freely movable surrounded by a heat shield 35. The cooling head 34 has a feeding water line 36 and an outletting water line 37 through which the coolant water flows. A further feeding water cooling pipe 38 is provided within the cooling path 33 and below the insulation area 29. The corresponding outletting water cooling pipe is not visible in FIG. 2 since it is hidden by the water cooling pipe 38. The cooling with the aid of the water cooling pipe 38 is required, so that if a mold shell 39 is lowered in which the melting material 21 is located the temperature gradient is set in a defined way through radiation of the heat in the mold shell 39.

The melt 21 is let into the casting mold or mold shell 39 respectively by means of a pouring funnel 40 which has a relatively long tube 41 with a small opening 42, which casting mold or mold shell 39 comprises an upper funnel-shaped structure 43 and a lower tube 44 which is disposed above the cooling head 34. Between the funnel-shaped structure 43 and the tube 44 a ceramic filter 45 is disposed which after the pouring in of the melt 21 is still covered with this melt 21. Instead of a tube 44 a casting mold can also be provided having any given other geometry, for example the geometry of a turbine bucket. The casting mold or mold shell 39 comprised preferably of a ceramic substance which is destroyed after the casting process.

The melt 21 itself in FIG. 2 is subdivided into three areas: into a zone 46 with liquid metal, a zone 47 with solidified metal, and a zone 48 in which the metal is just solidifying. With the aid of an electron-optical image converter 49 known per se located in a heat protection enclosure 51 closed off with a protective glass which projects into the vacuum oven, the casting mold surface adjacent to the solidification zone 48 as well as the area lying above and below is detected. An infrared lens system 52 images the total detected area as infrared image 53 on a photocathode 54. From this photocathode 54 depending on the intensity of the impingeing radiation more or less free electrons are emitted. By using highly sensitive multi-alkali cathodes the sensitivity range can be extended to approximately 1.3 μm. The free electrons coming from the photocathode 54 are accelerated through the electrical field of an electron lens system 56 so that their energy on impingeing on a luminescent screen 57 is sufficient to generate a visible image 58. This image 58 can now be viewed with an eyepiece or be evaluated electronically. It is understood that the electron-optical image converter is selected only as example for a device which reproduces the area around the solidification zone as heat image. It is also possible to use an evaporograph, a special vidicon television recording tube, a pyroelectrical heat image tube, an optomechanical scanning system or another infrared camera.

Figure 3:
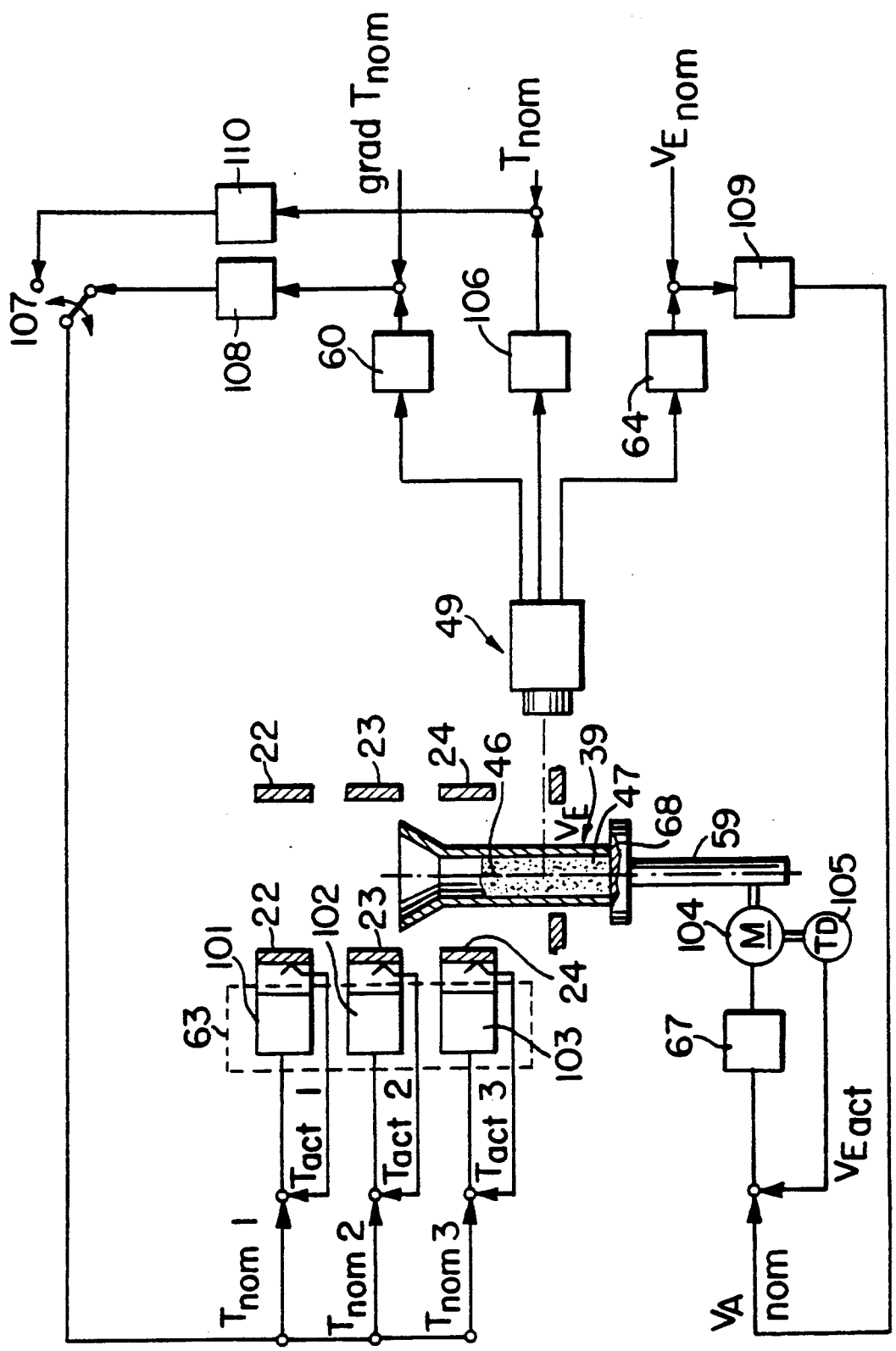
FIG. 3 a fundamental representation of the regulation scheme including the infrared camera which monitors the phase transition of the melt.

In FIG. 3 an arrangement according to the invention is represented with which it is possible to carry out a control of the melt in a vacuum oven or the like using a thermocamera. This arrangement has a device 60 with which it is possible to determine the temperature gradients along the Z-axis (FIG. 1). For the determination of a gradient it is not required to know the absolute values; it is sufficient if the difference values are determined. Difference value formation with images constructed of points or pixels are known for example in the field of autofocus cameras (cf. U.S. Pat. No. 4,218,119, FIG. 2 to 5). There the brightness differences of adjacent points are determined in order to calculate the contrast which signifies whether an image is set sharp (=high contrast) or not sharp (=low contrast). This method known from the autofocus technique can also be applied in the present case to determine the temperature gradient. Moreover, it is even possible with the help of a thermocamera to make statements regarding the absolute temperatures.

Infrared cameras in contrast to conventional radiation thermometers are most often not equipped with a direct display of a voltage corresponding to the temperature of a black radiator as reference value. With the aid of a setting regulator for isotherms which is provided with a precise scale, differences of the output voltages $S_m$ of two different measuring points can however be determined. For radiation measurements with pyrometers the fundamental equation can be applied generally $$S_m = S_w(1-\epsilon)S_u$$

where $S_m$ signifies the output voltage of a pyrometer which is directed toward a black radiator ($\epsilon = 1$) with temperature $T_m$. $T_m$ is the temperature actually indicated by the pyrometer at an emission degree setting to $\epsilon = 1$. $S_w$ is the output voltage of a pyrometer directed toward a black radiator ($\epsilon = 1$) with temperature $T_w$. $T_w$ is the true temperature of the measured object. $S_u$ is the output voltage of a pyrometer directed to the surroundings which is also measured through the reflection at the surface of the measured object, which, as a rule, is the wall of the measuring room. $T_u$ is the measured temperature of the surroundings, thus the measuring room wall, while $\epsilon$ denotes the degree of emission of the measured object.

Thus, if with an infrared camera a reference site of known temperature and known degree of emission is also measured, it is possible by means of the setting regulator to determine precisely the absolute temperature of a measured object. If the isotherms of the camera are first set to the measured object with the true temperature $T_{w1}$ and the degree of emission $\epsilon_1$ and subsequently to the reference site with the true temperature $T_{w2}$ with the degree of emission 2, a voltage difference $$\Delta S_m = S_{m1} - S_{m2} = \epsilon_1 S_{w1} + (1-\epsilon_1)S_u - [\epsilon_2 S_{w2} + (1-\epsilon_2)S_u]$$

is obtained wherefrom follows $$\Delta S_m = \epsilon_1[S_{w1} - S_u] - \epsilon_2[S_{w2} - S_u].$$

In practice it is very often only required to determine the temperature distribution on the surface of a particular object. If the temperature at a particular site of the object is known, this site can be used as reference. Since the degree of emission of the surface of the measured object can be seen in many cases as being constant the above equation can be simplified for $\epsilon_1 = \epsilon_2 = \epsilon$ to $$\Delta S_m = \epsilon[S_{w1} - S_{w2}].$$

The temperature determination is thereby independent of the ambient temperature $T_u$. With known degree of emission the temperature difference $\Delta T_w = T_{w1} - T_{w2}$ can be determined rapidly and readily with the aid of a calibrated curve or a nomogram established for the IR camera from the measured difference of the isotherm values $\Delta S_m$.

The arrangement according to FIG. 3, apart from the already cited device 60 for the determination of the temperature gradient, has in addition a device 106 which on the basis of signals from the thermocamera 49 determines the actual temperature $T_{act}$ at a point as well as a further device 64 which from data from the thermocamera 49 determines the actual solidification front $V_{Eact}$. With the aid of a grad T-regulator 108, which is acted upon by the difference of nominal and actual value of grad T, via a switch 107 heating windings 22, 23, 24 are acted upon via heating-proportion regulator 63 with the nominal temperature $T_{nom1}$ or $T_{nom2}$ or $T_{nom3}$ respectively. With the switch 107 it is possible to switch over from the grad T-regulator 108 to a T-regulator 110 which is acted upon by the difference between $T_{nom}$ and $T_{act}$. The difference of $V_{Eact}$ and $V_{Enom}$ is given on a $V_E$ regulator 109 which outputs an output signal which is compared with $V_{Eact}$ and serves for driving a motor regulator 67 which drives the motor 104. The magnitude of $V_{Eact}$ is determined by means of a tachodynamo 105 connected with the motor 104 which moves the relocatable rod 59 on which is disposed the cooling plate 68.

With the arrangement according to FIG. 3 it is consequently possible using the thermocamera 49 to set the vertically progressing solidification zone 48 so as to be advancing or trailing through appropriate pulling-off of the cooling plate 68 by means of motor 104 quasi-stationary or to influence the crystallization in the area of the cooling path 33 and to influence the temperature gradient or the temperature typical for the solidification zone—by switching over by means of switch 107—at this site via the heating devices 101 to 103.

The thermocamera 49 observes the temperature conditions reflected on the casting mold 39 of the melt inside of it. Through appropriate setting of the image area of the camera temperature points of a sufficiently large number can be determined in the vertical direction and therefrom through difference formation over the distances of the measuring points the corresponding temperature gradients can be formed as has already been described in connection with FIG. 1b.

By means of the solidification temperature and the temperature gradient the transition zone solid/liquid can be determined as well as also their progression in time which corresponds to the solidification velocity $V_E$. The actual value $V_{Eact}$ determined by the device 64 from the data of the thermocamera 49, is compared with the nominal value of the solidification velocity $V_{Enom}$ and supplied to the regulator 109 whose output is connected with the motor regulator 67 setting the pull-off velocity $V_A$. The pull-off velocity $V_A$ is regulated so that the solidification zone 48 is located as much as possible at a desired site of the cooling path 33.

Based on the possibility of the thermocamera 49 to measure many points within its area of view simultaneously, a relationship of the temperature points to the position of the solidification zone can also be derived. By means of the nominal value of the temperature gradient supplied by device 60 or of the nominal value of the temperature itself supplied by the device 106 the gradient can be effected via the heating regulators 101 to 103.

Figure 4:
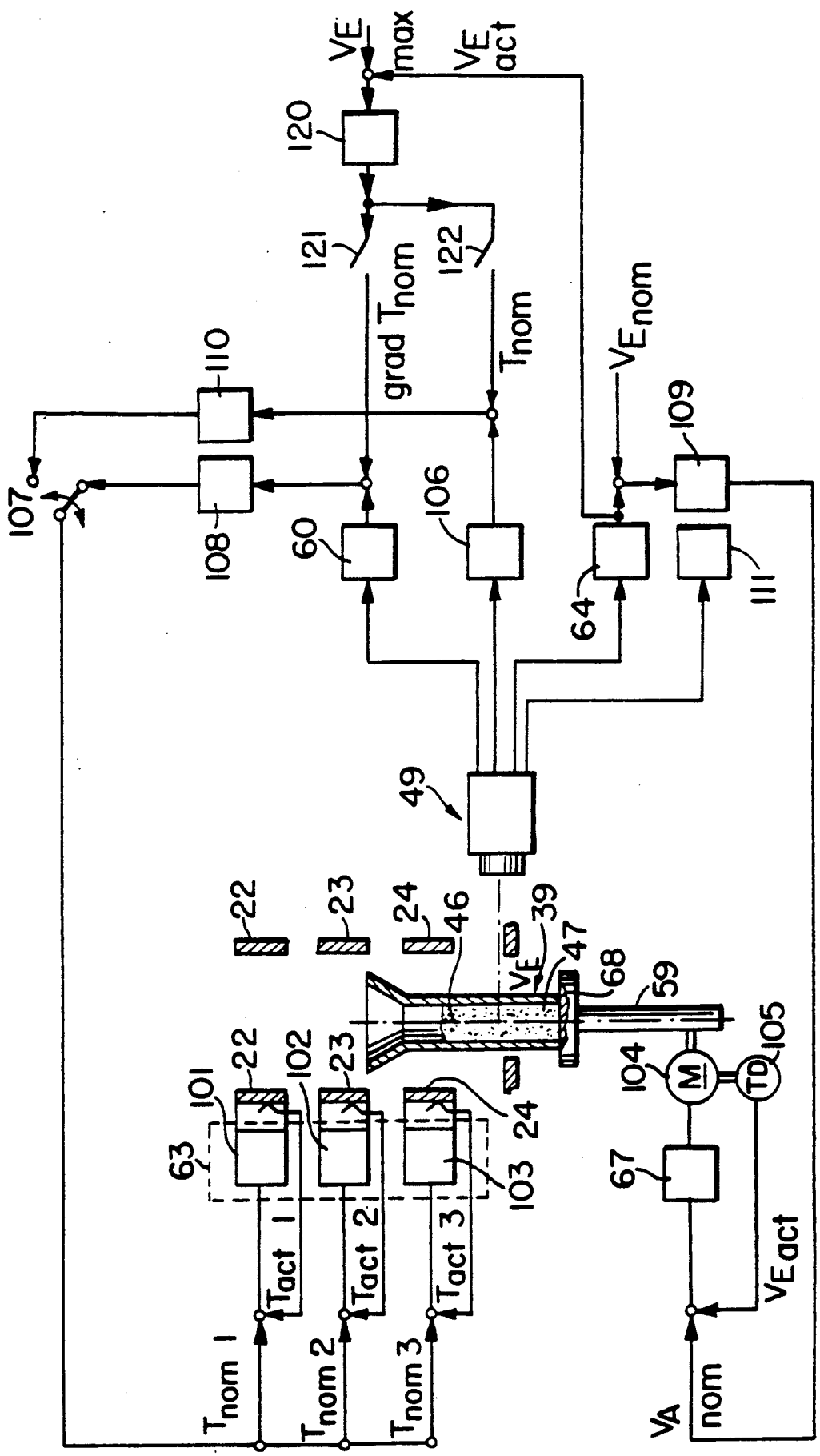
FIG. 4 an arrangement with which the solidification zone can be set.

A variant of the arrangement according to FIG. 3 is shown in FIG. 4. With this arrangement it is possible to adjust the heating system only upon exceeding a given solidification velocity. To this end a $V_E$-release-regulator regulator 120 is provided onto whose input the difference of $V_{Emax}$ and $V_{Eact}$ is placed and which supplies via a switch 121 grad $T_{nom}$ or via switch 122 $T_{nom}$. To the thermocamera 49 is additionally connected a device 111 for the determination of the spatial coordinates of the solidification front.

A lowering of the rod 59 and the cooling plate 68 and consequently the casting mold 39 effects that the melt is moved away from the heating device 22, 23, 24 while a raising of rod 59 and cooling plate 68 brings the melt into the vicinity of the heating device 22, 23, 24. The cooling off of the entire melt in the casting mold 39 is greater the greater the thermal gradient and the greater the lowering velocity.

With the application of optical methods for the detection of the temperatures of a casting piece essentially two problems result: the problem of the temperature differences over the thickness of the mold shell 39 and the problem of the scattered light which reaches from the heating elements 22 to 24 directly to the outside of the mold shell 39.

The first-mentioned problem originates thereby that between the internal and the external side of the mold shell 39 temperature differences occur whereby the outside temperature detected by the thermocamera 49 does not reflect the inside temperature precisely. Even in the case of thin shells temperature differences of from 40° to 70° C. occur, i.e. a direct assignment between surface temperature and the temperature of the cast piece is virtually not possible.

However, this problem can be circumvented if from the measured surface temperature with the aid of the local mold shell thickness and by means of the coefficient of emission one calculates back to the temperature of the casting piece. Since variations of thickness of the mold shell due to fabrication tolerances and uncontrolled changes of the coefficient of emission are not eliminatable in this manner, it is important to use mold shells produced with a high degree of precision. Another possibility comprises is detecting through a thermoelectric couple or the like the actual temperature of the melt at one point and to reference the temperature determined by the thermocamera through this actual value, i.e. to increase it as a rule by a constant amount. It is therein important that the temperatures on the outside of the mold shell represent a precise reflection of the temperatures on the inside shifted only by a constant scaling factor. A distortion of the reflection in the vertical direction which can lead to measurement errors can largely be avoided thereby that the mold shell 39 has a good thermal conductivity or at least is structured in the manner of a sandwich in the vertical direction wherein a layer having good thermal conductivity is adjoined by a layer having poor thermal conductivity. As mold shell material highly refractory metals or metal alloys are possible which can be lined on the inside by a ceramic layer so that no chemical reaction occurs between the mold shell material and the melt.

The problem of the scattered light originates by the fact that the temperature of the outside of the mold shell 39 indicated by radiation comprises two components:

that component which is generated due to the through-radiation of the melt to the outer wall of the mold shell 39, and that component generated due to the direct radiation of the heating elements 22 to 24 onto the outer wall of the mold shell 39. The thermocamera 49 will determine due to this direct irradiation a higher temperature on the outside of the mold shell 39 than corresponds to the inside temperature of the melt. To compensate for this error it is possible to eliminate through appropriate optical filters in front of the lens of the thermocamera 49 the influence of the direct irradiation of the heating elements 22 to 24. The radiation curve $S=f(\lambda)$ of the heating elements 22 to 24 differs from the radiation curve $S'=f(\lambda)$ generated by the melt so that by means of a filter $S=f(\lambda)$ can be filtered out and only a radiation range remains stemming from the melt.

It is known that the surface temperature of a radiating body can be determined, on the one hand, from the absolute intensity of the radiation given off and, on the other hand, from the ratio of the intensities from two or more wave lengths. This fact can be used in the invention to the effect that two or more wavelengths characteristic for the radiation of the melt and not for the radiation of the heating elements are possible filtered out with the aid of interference filters and are drawn on for the temperature reference. It is further possible to record with the thermocamera calibration curves of different crucible-melt combinations and to store them in a computer or the like. After the melt has been brought to its highest temperture these calibration curves are recorded with the heating system switched off so that no scattered light occurs.

I claim:

1. An improved device for maintaining at a predetermined height the solid liquid interface of a metal or metal alloy melt in a container (39) by means of a thermal camera which images a predetermined planar area of the container, said device comprising:
    a) heating means (22 to 24) and cooling means (69) for controlling the position of the interface;
    b) first means (60, 106) for comparing data from at least two points in the area imaged by the thermal camera (49) and for determining, as result of the comparison, the thermal gradient along at least one coordinate of the container (39);
    c) second means (64) responsive to the data supplied by the thermal camera (49) for determining the solidification velocity of the melt along at least one coordinate of the container (39); and
    d) third means (101 to 103) responsive to either the thermal gradient or the temperature and the solidification velocity for controlling the heating means (22 to 24) and the cooling means (68).

2. Device as stated in claim 1, wherein a fourth means (106) is provided which on the basis of data supplied by the thermal camera (49) determines within its field of view the temperature at any given point of the container (39) and assigns it to the measuring site.

3. Device as stated in claim 1, wherein a fifth means (109) is provided which on the basis of data supplied by the thermal camera (49) detects the positions of particular sites of the measuring field.

4. Device as stated in claim 1, further including means for determining the thermal gradient, said means including means for line-wise scanning of the image imaged on the surface (54) and comparison of successive lines.

5. Device as stated in claim 1, further including means for determining the thermal gradient, said means including means for point-wise scanning of the image imaged on the surface (54) and comparison of successive points.

6. Device as stated in claim 1, further including means for determining the solidification velocity, said means including means for repeatedly detecting the position of the phase boundary (48) along at least one coordinate and means for forming the quotient from at least two positions and the time elapsed from the transition from the one into the other position.

7. Device as stated in claim 1, wherein a heating temperature regulator (62) is provided which sets a heating temperature as a function of the difference between nominal temperature gradient and actual temperature gradient.

8. Device as stated in claim 7, wherein a heating-proportion regulator (63) is provided which distributes the temperature set by the heating temperature regulator (62) onto at least two heating windings (22, 23).

9. Device as stated in claim 4, wherein a device (66) for the setting of the solidification velocity of the cooling device (68) is provided.

10. Device as stated in claim 1, wherein an arrangement (50, 51) is provided for the screening of the thermal camera (49) against disturbing heat and infrared light sources.

11. Device as stated in claim 1, further including means for forming the product of solidification velocity and temperature gradient.

12. Device as stated in claim 1, wherein the thermal camera (49) is disposed above the cooling device (33, 68).

13. Device as stated in claim 1, wherein a vertically relocatable rod (59) with a cooling plate (68) is provided on which is disposed a casting mold (39) which can be moved past a heating device (22, 23, 24) which on the basis of data from the thermal camera (49) can be heated to a lesser or greater degree.

14. Device as stated in claim 13, wherein the vertical drive of the rod (59) and the heating by the heating device (22, 23, 24) take place so that a given solidification proportion of a metal or metal alloy is achieved.

15. Device as stated in claim, 13 wherein the thermal camera (49) contains an optical filter which passes through only that radiation which is emitted by the material contained in the casting mold (39) while it filters out that radiation stemming from the heating device (22 to 24) or other disturbance radiation sources.

16. Device as stated in claim 1, wherein the casting mold (39) is comprised of a material which is a good thermal conductor and that the inner wall of the casting mold is lined with a ceramic material.

17. Device as stated in claim 1, further including means for converting the temperatures detected by the thermal camera (49) of the outside of the casting mold (39), in partial response to the known thickness and the known radiation characteristics of the casting mold (39), to the actual temperatures of the material within the casting mold (39).

18. Device as stated in claim 1, wherein the casting mold (39) is structured in the manner of a sandwich in the vertical direction wherein a layer of poor thermal conductivity is followed by a layer of good thermal conductivity.

19. Device as stated in claim 1, wherein the actual temperature of the melt is detected at a point by means of a thermoelectric couple and that this detected temperature is used as reference variable.

20. Device as stated in claim 1, wherein with the melt heated and the heating system (22 to 24) switched off calibration curves with the aid of the thermal camera (49) are recorded and stored and are stored.

* * * * *